United States Patent [19]

Sakakibara et al.

[11] 4,277,393
[45] Jul. 7, 1981

[54] RADIOIMMUNOASSAY METHOD FOR DETERMINING CALCITONIN AND RADIOACTIVE TRACER FOR USE THEREIN

[75] Inventors: Shumpei Sakakibara, Suita; Yuichi Kumahara, Toyonaka; Yoshiaki Okada, Takatsuki; Hiroshi Ogawa, Kashiwa; Nobuhiko Nakazawa, Narita; Shoichiro Tsushima, Ichikawa, all of Japan

[73] Assignee: Daiichi Radioisotope Laboratories, Ltd., Tokyo, Japan

[21] Appl. No.: 951,813

[22] Filed: Oct. 16, 1978

Related U.S. Application Data

[63] Continuation-in-part of Ser. No. 910,559, May 30, 1978, abandoned.

[30] Foreign Application Priority Data

Jun. 20, 1977 [JP] Japan .................................. 52/73130

[51] Int. Cl.³ .................... C07C 103/52; G01N 33/00; G01N 33/48
[52] U.S. Cl. .............................. 260/112.5 R; 424/1.5
[58] Field of Search ................... 260/112.5 R; 424/1.5

[56] References Cited

U.S. PATENT DOCUMENTS 3,997,525  12/1976  Guy ...................................... 424/182

FOREIGN PATENT DOCUMENTS 2826844  12/1978  Fed. Rep. of Germany .... 260/112.5 R

OTHER PUBLICATIONS

G. Erle, et al., Horm. Metab. Res. 5 (1973) 230.
R. J. De Bruin, et al., Chem. Abstr. 79, 1973, 39854n.
O. K. Behrens, et al., Ann. Rev. Biochen 38, (1969) 83–112.
"The Pharmacological Basis of Therapeutic's" p. 254.

*Primary Examiner*—Delbert R. Phillips
*Attorney, Agent, or Firm*—Sughrue, Rothwell, Mion, Zinn and Macpeak

[57] ABSTRACT

A hentriacontapeptide of the formula (I)

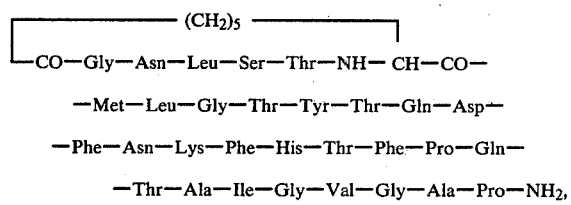

—Met—Leu—Gly—Thr—Tyr—Thr—Gln—Asp—

—Phe—Asn—Lys—Phe—His—Thr—Phe—Pro—Gln—

—Thr—Ala—Ile—Gly—Val—Gly—Ala—Pro—NH$_2$, a radioactive labeled hentriacontapeptide of the formula (I), useful in a radioimmunoassay method and a radioimmunoassay method for determining calcitonin.

1 Claim, 5 Drawing Figures

ELUTION PATTERN
(SEPHADEX G 50)

RADIOIMMUNOASSAY METHOD FOR DETERMINING CALCITONIN AND RADIOACTIVE TRACER FOR USE THEREIN

CROSS-REFERENCE TO RELATED APPLICATIONS

This application is a continuation-in-part application of copending application Ser. No. 910,559, filed May 30, 1978, now abandoned.

BACKGROUND OF THE INVENTION

1. Field of the Invention

This invention relates to a method for radioimmunoassay (hereinafter RIA) of calcitonin, to a radioactive-iodine labeled tracer for use therein, and to a process for preparing the tracer.

2. Description of the Prior Art

Calcitonin, a peptide hormone, has an effect on the metabolism of calcium and human calcitonin was isolated in 1968 from the tumor tissue of a patient with medullary carcinoma of the thyroid.

The amino acid sequence of human calcitonin was determined also in 1968 as

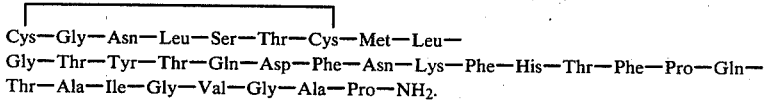

An antibody to calcitonin was prepared using native calcitonin as an antigen obtained from the extract of medullary carcinoma of the thyroid as described in Clark et al., *Lancet*, 74 (1969) while an antibody using synthetic human calcitonin was prepared and then a radioimmunoassay method was developed as described in Frölich et al., *Horm. Metab. Res.*, 3 297 (1971). However, some important problems remain unsolved in their radioimmunoassay.

When the extract of medullary carcinoma of the thyroid is used as the source of calcitonin, contamination by some polymers in calcitonin is observed as described in Neher et al., *Nature*, 220 984 (1968). Therefore, the serum level obtained by the radioimmunoassay does not necessarily indicate the true value.

On the other hand, synthetic and native calcitonin have a disulfide bond in the molecule, and the bond is subject to chemical change. It has been confirmed that the biological activity of calcitonin substantially disappeares due to the rupture of the disulfide bond.

Further, when native or synthetic calcitonin is labeled with radioactive iodine, some polymerized materials are present as contaminants in the product. Thus, actually available labeled calcitonin should be obtained using certain complicated purification procedures. Moreover, H. Tashjian et al., *Endocrinol.*, 84 140 (1969) discloses that calcitonin labeled with radioactive iodine is unstable and tends to be inactivated during storage.

SUMMARY OF THE INVENTION

Therefore, an object of the present invention is to provide a superior radioimmunoassay method for determining calcitonin.

Another object of this invention is to provide a calcitonin material, which, when radioactively labeled, can be used in a radioimmunoassay method for determining calcitonin.

A further object of this invention is to provide a stable radioactive tracer material for use in determining calcitonin.

Accordingly, this invention provides a hentriacontapeptide of the formula (I), which is a partially modified calcitonin,

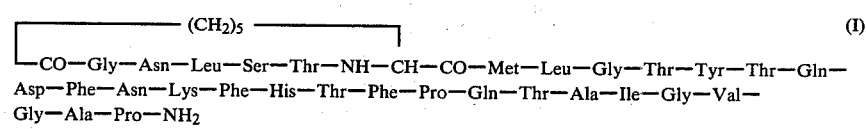

wherein the indication of the amino acid residues are based on the abbreviations used in general and, except for the glycine, all of the amino acids are the L-form thereof. The term "hentriacontapeptide" will be used throughout this specification to designate the peptide of the formula (I) unless otherwise indicated.

This invention in another embodiment provides a radioactive iodine labeled hentriacontapeptide of the formula (I) useful as a tracer in the determination of calcitonin.

This invention in an even further embodiment provides a radioimmunoassay method for determining calcitonin comprising incubating a sample containing calcitonin, an antibody to calcitonin and a radioactive tracer, separating antibody-bound radioactive tracer from free radioactive tracer and measuring the radioactivity of the antibody-bound radioactive tracer or the free radioactive tracer, wherein the improvement comprises the radioactive tracer is the radioactive iodine labeled hentriacontapeptide of the formula (I) above.

DETAILED DESCRIPTION OF THE INVENTION

The hentriacontapeptide of the formula (I) above can be prepared by the method described below and is useful in the determination of calcitonin by radioimmunoassay because the labeled hentriacontapeptide is stable since no disulfide bond is present in the peptide chain and it behaves substantially the same as human calcitonin in the antigen-antibody reaction.

That is, when the hentriacontapeptide is labeled at the tyrosine moiety thereof with radioactive iodine, it reacts with an antibody to calcitonin equally to the standard material or the human calcitonin in the serum. The antibody to calcitonin can be produced by immunization of an animal with calcitonin, however, the synthetic hentriacontapeptide can be also used and is advantageous from the standpoint of its stability. In order to produce the antibody, known methods can be used as described, e.g., in *Steroids*, 23 49 (1974), ibid., 23 203 (1974), etc. For example, from 50 μg to 1,000 μg of the hentriacontapeptide is dissolved in from 0.5 to 1 ml of physiological saline or an acidic solution containing a mineral acid, e.g., 0.01 N hydrochloric acid or an organic acid, e.g., 0.1 N acetic acid. An equal or excess volume of an adjuvant, such as complete Freund's adjuvant, is then mixed with the solution. The mixture is emulsified and administered to an animal, e.g., rabbits, goats, sheep, guinea pigs and the like. The administration can be by intradermal, subcutaneous, intramuscular or intraperitoneal injection. About 50 μl of the emulsion is administered at multiple sites of the animal. Then, booster immunizations are made at intervals of from two weeks to two months and, 7 days to 14 days after the booster, the blood is collected and anti-serum can be obtained therefrom using conventional methods.

The radioactive tracer which can be used in the radioimmunoassay method of this invention can be prepared from the hentriacontapeptide of the formula (I) as described below.

To 2 to 5 μg of the hentriacontapeptide (5 μl), 10 to 30 μl of a 0.4 M phosphate buffer solution (pH 6.0–7.5) is added and 0.5 to 2 mCi of a radioactive sodium iodide, for example, Na$^{125}$I, is added thereto. Then, 10 μl of a solution containing 2 to 20 μg of chloramine T is added and reacted at 25° C. The reaction is completed in a period of 5 to 30 seconds which varies depending on the acidity of the solution and the reaction can be stopped by addition of 20 to 40 μl of a solution containing 5 to 100 μg of sodium metabisulfite.

Through the method described above, $^{125}$I-labeled-hentriacontapeptide with a specific radioactivity of from 100 μCi/μg to 500 μCi/μg is obtained. The $^{125}$I-labeled-hentriacontapeptide can be stored in a lyophilized form which is produced by addition of a phosphate buffer solution containing bovine serum albumin (hereinafter BSA for brevity) and freeze-drying the resultant mixture.

Figure 1:
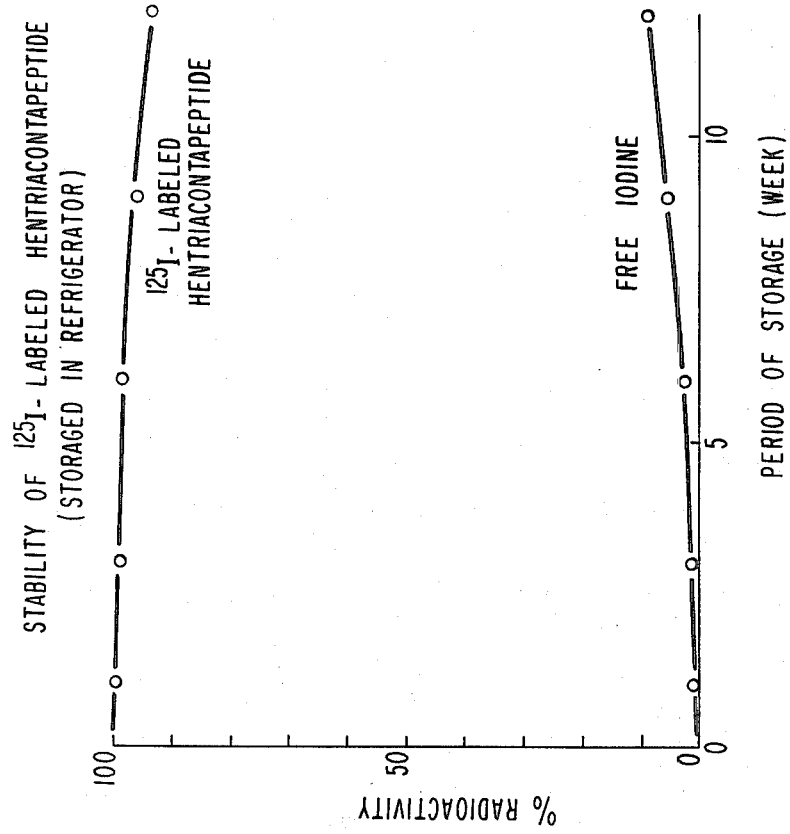
FIG. 1 shows the stability of $^{125}$I-labeled hentriacontapeptide.

The $^{125}$I-labeled-hentriacontapeptide is stable as shown in FIG. 1 and the stability thereof was evaluated in the following manner.

1 ml of a phosphate buffer solution containing about 2 μCi of $^{125}$I-labeled-hentriacontapeptide was placed into a vial and freeze-dried. Then, the air in the vial was replaced with nitrogen and the vial sealed, which was used for testing. The lyophilizate was dissolved in 2 ml of distilled water and 200 μl of the solution was added to a column (1×40 cm) packed with Sephadex G 50 (trade name, produced by Pharmacia Fine Chemicals). This was eluted with a 0.05 M phosphate buffer solution (pH 7.5) containing 0.5% BSA. The material eluted in the 20–35 ml fractions is considered to be $^{125}$I-labeled-hentriacontapeptide and in the 35–50 ml fractions to be free iodine, then the ratio of the two is calculated. As described above, the result is shown in FIG. 1 which indicates that the tracer has excellent stability.

The radioimmunoassay method of this invention can be conducted adapting techniques and procedures described in, e.g., *Anal. Lett.*, 5 757 (1972), ibid., 5 767 (1972), *Journal of Analytical Endocrinology and Metabolism*, 35 219 (1972), G. E. Abraham, "Radioimmunoassay of Plasma Steroid Hormones", *Modern Methods of Steroid Analysis*, Chap. 21, Academic Press, New York and London (1973), *The Japanese Journal of Nuclear Medicine*, 12 123 (1975), *Clinica Chimica Acta*, 66 319 (1976), and *Steroid Immunoassay*, E. H. D. Cameron Ed., Alpha Omega Publishing Ltd., Cardiff. Wales U.K. (1975), wherein the improvement comprises using the radioactive iodine-labeled-hentriacontapeptide of this invention. More specifically, the radioactive iodine-labeled-hentriacontapeptide (tracer) and an antiserum are added to a standard material or to a sample to be tested and the mixture is incubated at 4° to 37° C. Then, the antiserum-bound radioactive tracer is separated from the free tracer (bound/free (BF) separation) and the radioactivity of the bound tracer or the free tracer is counted.

For BF separation, various methods described in the above references can be used and the double antibody method or the solid phase method are preferred techniques. Application of these methods to this invention are described below.

(i) Double Antibody Method

A sample (or a standard solution), a tracer and an antiserum were reacted and to the reaction mixture, 0.3 to 1.0% of normal rabbit serum as a carrier-protein, a goat antiserum produced by immunization of goats with rabbit gamma globulin is added and the mixture is allowed to stand at room temperature (e.g., 25° C., hereinafter the same) for several hours or at 2° to 8° C. overnight, then the insoluble materials are separated by centrifugation at room temperature or low temperature, e.g., 2° to 8° C. After removal of the supernatant, the radioactivity of the precipitate is counted using conventional methods, e.g., using a scintillation counter.

(ii) Solid Phase Method

The test sample or the standard solution and the tracer are added to an anti-serum coupled with an appropriate matrix to react. Suitable anti-serum coupled matrices include mainly (a) test tubes coated with synthetic resins, such as polyethylene, polystyrene, polypropylene and the like, (b) a glass test tube or glass beads, (c) a disc or a cup formed of synthetic resins, such as polyethylene, polystyrene, polypropylene and the like.

After the reaction has been completed, the reaction mixture is removed and the radioactivity of the tracer coupled with the antiserum on the surface of the matrix is counted using conventional methods, e.g., using a scintillation counter. Human calcitonin can be used as the standard material, but it is advantageous to use the hentriacontapeptide from the standpoint of stability.

The method of preparing the hentriacontapeptide of the formula (I) is described in detail in Example I below. The preparation of the starting materials used in Example I is shown in Example II below. The method for preparing the radioactive labeled-material of this invention, the method for production of calcitonin antibody, and the radioimmunoassay method are described in detail, respectively, in Examples III, IV and V below.

In the Examples given below, all percents are by weight unless otherwise indicated and the abbreviations used in the specification and in the Examples given hereinafter have the following meanings.

| | |
|---|---|
| BOC | t-Butoxycarbonyl |
| AOC | t-Amyloxycarbonyl |
| Bzl | Benzyl |
| Bzl(Cl$_2$) | Dichlorobenzyl |
| Cbz | Benzyloxycarbonyl |
| Cbz(o-Cl) | o-Chlorobenzyloxycarbonyl |
| OBu | t-Butyl ester |
| OEt | Ethyl ester |
| OBzl | Benzyl ester |
| ONP | p-Nitrophenyl ester |
| OSU | N-Hydroxysuccinimide ester |
| TFA | Trifluoroacetic acid |
| TosOH | p-Toluenesulfonic acid |
| CHA | Cyclohexylamine |
| DCHA | Dicyclohexylamine |
| THF | Tetrahydrofuran |
| DMF | Dimethylformamide |
| DCC | Dicyclohexylcarbodiimide |
| WSC | N-Ethyl-N'-dimethylaminopropyl-carbodiimide |
| HOSU | N-Hydroxysuccinimide |
| HOBT | 1-Hydroxybenzotriazole |
| BuOH | Butanol |
| HMPA | Hexamethylphosphoric triamide |
| MeOH | Methanol |
| EtOH | Ethanol |
| AcOH | Acetic acid |
| Ser | L-Serine |
| Asn | L-Asparagine |
| Leu | L-Leucine |
| Thr | L-Threonine |
| Val | L-Valine |
| Met | L-Methionine |
| Asp | L-Aspartic acid |
| Phe | L-Phenylalanine |
| Gly | Glycine |
| Lys | L-Lysine |
| Gln | L-Glutamine |
| Ile | L-Isoleucine |
| Ala | L-Alanine |
| His | L-Histidine |
| Tyr | L-Tyrosine |
| Pro | L-Proline |

EXAMPLE I

Porudiction of Hentriacontapeptide of the Formula

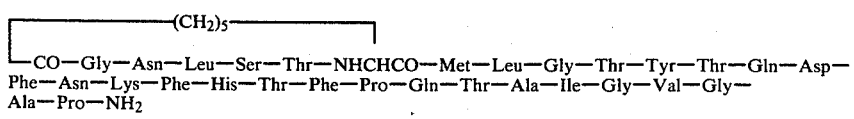
—CO—Gly—Asn—Leu—Ser—Thr—NHCHCO—Met—Leu—Gly—Thr—Tyr—Thr—Gln—Asp—Phe—Asn—Lys—Phe—His—Thr—Phe—Pro—Gln—Thr—Ala—Ile—Gly—Val—Gly—Ala—Pro—NH$_2$ BOC-Thr(Bzl)-Thr[Bzl(Cl$_2$)]-Thr(Bzl)-Gln-Asp(OBzl)-Phe Asn-Lys[Cbz(o-Cl)]-Phe-His-Thr(Bzl)-Phe-Pro-Gln-Thr(Bzl)-Ala-Ile-Gly-Val-Gly-Ala-Pro-NH$_2$ (2.0 g, 0.6 mmol) was cooled to −5° C. and 10 ml of TFA was added thereto. The mixture was stirred at room temperature for 30 minutes. After the reaction, the TFA was removed by concentration in vacuo and diethyl ether was added to the residue. The precipitates formed were collected by decantation and dried in a desiccator over sodium hydroxide. The precipitates were dissolved in 10 ml of DMF and the pH of the solution was adjusted to about 9 by addition of triethylamine under cooling. Water was then added to the solution and the precipitates formed were collected by filtration, washed with water and dried in a desiccator over phosphorus pentachloride to obtain the free base of the starting material (the BOC group was removed).

Separately, 122 mg of HOSU was added to a solution of 0.8 g (0.71 mmol) of

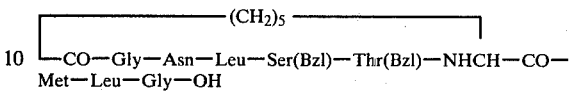
—CO—Gly—Asn—Leu—Ser(Bzl)—Thr(Bzl)—NHCH—CO—Met—Leu—Gly—OH dissolved in 5 ml of a mixed solution of DMF and N-methylpyrrolidone (1:1 by volume). Further, 146 mg of DCC dissolved in 3 ml of DMF was added thereto under cooling and then the mixture was reacted overnight. After the reaction, the precipitates formed were removed by filtration. The free base prepared as described above and 100 mg of HOBT were added to the filtrate and the mixture was stirred at 30° C. for 5 days. After the reaction, water was added to the reaction mixture and the precipitates formed were collected by filtration, washed with water and dried to obtain 2.6 g of crude powder of the formula:

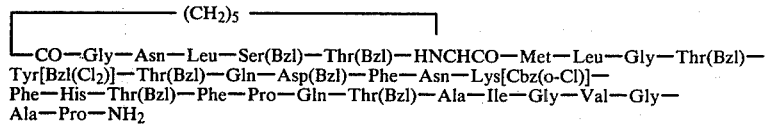
—CO—Gly—Asn—Leu—Ser(Bzl)—Thr(Bzl)—HNCHCO—Met—Leu—Gly—Thr(Bzl)—Tyr[Bzl(Cl$_2$)]—Thr(Bzl)—Gln—Asp(Bzl)—Phe—Asn—Lys[Cbz(o-Cl)]—Phe—His—Thr(Bzl)—Phe—Pro—Gln—Thr(Bzl)—Ala—Ile—Gly—Val—Gly—Ala—Pro—NH$_2$ 1.0 g of the crude powder prepared as described above, 0.1 g of methionine and 2 ml of anisole were placed in a tube in which hydrogen fluoride could be used as a reactant. Dimethyl thioether was added under reduced pressure and 25 ml of hydrogen fluoride was added under cooling with dry ice-methanol. Following this, the reaction was carried out at −5° C. for 60 minutes and after the reaction, the hydrogen fluoride was distilled off. Diethyl ether was added to the residue and the precipitates formed were collected by decantation. After washing the precipitates three times by decantation, the precipitates were dissolved in a solvent mixture containing 30 ml of acetic acid and 10 ml of water. The solution is passed through a column (2.5×8 cm) packed with Dowex 1×2 (acetic acid type) (trade name, produced by Dow Chemicals) and eluted with 200 ml of water. The eluate obtained was introduced into a column (2.5×7 cm) packed with Dianon HP 20 (trade name, produced by Mitsubishi Chemical). The column was then eluted with aqueous ethanol (80% by volume) and the ethanol was distilled off from the eluate. The resultant residue was freeze-dried to obtain 440 mg of powder. The powder was dissolved in a 0.01 M ammonium acetate aqueous solution and passed into a column (2.2×25 cm) packed with carboxymethyl cellulose. The column was eluted employing the linear concentration gradient method using 750 ml of a 0.01 M ammonium acetate aqueous solution (pH 4.5) and 750 ml of a 0.2 M ammonium acetate aqueous solution (pH 4.5). The eluate was collected as 10 g fractions and the active fractions (No. 67-70) were combined and freeze-dried. The powder obtained was dissolved in 1 M acetic acid, passed into a column (2.2 × 137 cm) packed with Sephadex LH-20 (trade name, produced by Pharmacia Fine Chemicals) and eluted with 1 M acetic acid. The eluate was fractionally collected by 6 g and active fractions (No. 28-37) were combined and freeze-dried.

The powder was dissolved in a solvent mixture of butanol-acetic acid-water (B 4:1:5 by volume) and the solvent mixture was passed into a column (2.7 × 52 cm) which was packed with Sephadex G-25 (trade name, produced by Pharmacia Fine Chemicals) using the lower layer of the solvent mixture and the liquid was replaced by the upper layer of the solvent mixture. The column was eluted with the upper layer of the solvnt mixture and fractions of 6 g each were collected. The active fractions (No. 5-14) were combined and freeze-dried. The powder was chromatographed again with Sephadex G-25 under the same conditions as described above and the active fractions were collected and freeze-dried.

The powder was dissolved in 1 M acetic acid and the solution then passed into a column (2.2 × 137 cm) packed with Sephadex LH-20 and eluted with 1 M acetic acid. The eluate was collected as fractions of 5 g and the active fractions were combined and freeze-dried to obtain 29.7 mg (1,000 MRC unit/mg) of the desired product.

Analysis of the product was conducted with the following results being obtained.

Chromatographic Analysis

Rf=0.82 (carrier: cellulose, a product of Merck & Co.; developing solvent: n-butanol:acetic acid:water:pyridine (15:3:12:10 by volume)

Rf=0.43 carrier: cellulose, a product of Merck & Co.; developing solvent: n-butanol:acetic acid:water (4:1:5 by volume) upper layer)

Specific Optical Rotation $[\alpha]_D^{26}$ −69.6° (c=0.72, 1 M acetic acid)

Amino Acid Analysis

Lys 1.15(1), His 1.01(1), Asp 2.94(3), Thr 4.80(5), Ser. 1.06(1), Glu 2.14(2), Pro 1.96(2), Gly 4.00(4), Ala 2.00(2), Val 0.95(1), Met 0.87(1), Ile 0.96(1), Leu 1.84(2), Tyr 0.96(1), Phe 3.18(3), α-aminosuberic acid 1.02(1)

EXAMPLE II

The starting materials used in Example I above were prepared in the following manner.

(II-A) Production of Nonapeptide Fragment of the Formula

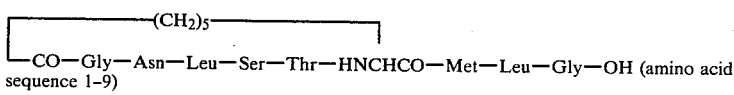

—CO—Gly—Asn—Leu—Ser—Thr—HNCHCO—Met—Leu—Gly—OH (amino acid sequence 1-9)

(1) Production of BOC-Leu-Gly-OBzl

BOC-Lue-OH (46.2 g), HOBT (1 g) and H-Gly-OBzl-Tos-OH (74 g) were suspended in a solvent mixture of 100 ml of DMF and 200 ml of dichloromethane. While cooling at −5° C., a solution of 34 g of WSC dissolved in 50 ml of dichloromethane was added dropwise thereto with stirring. After 1 hour, the reaction mixture was warmed to room temperature and stirred overnight. The dichloromethane was removed by concentration in vacuo, and water was added to the resultant DMF solution. The mixture was extracted with 1 liter of ethyl acetate and then with 500 ml of ethyl acetate. The ethyl acetate layer was washed with 1 N hydrochloric acid, water, a 5% sodium bicarbonate aqueous solution and water, dried over anhydrous sodium sulfate and concentrated in vacuo to obtain 82 g of oily BOC-Leu-Gly-OBzl.

(2) Production of BOC-Met-Leu-Gly-OBzl 1 liter of ethyl acetate was added to 150 g of BOC-Met-OH·DCHA. The mixture was washed, twice with 600 ml of 1 N sulfuric acid and with 500 ml of water, dried over anhydrous sodium sulfate and concentrated in vacuo. The residue was dissolved in a solvent mixture of 100 ml of dichloromethane and 100 ml of THF. After addition of 41 g of HOBT, the mixture was cooled to −5° C. and 62 g of DCC dissolved in 100 ml of dichloromethane was added dropwise thereto.

Separately, 300 ml of TFA was added to 137 g of BOC-Leu-Gly-OBzl while cooling to −5° C. and then the mixture was reacted for 30 minutes. After the TFA had been removed by evaporation in vacuo, the residue was dissolved in 75 ml of THF and the pH was adjusted to about 6.7-7 by addition of 155 ml of triethylamine under cooling with ice. The resultant solution was added dropwise to the dichloromethane solution of BOC-Met-OH prepared as described above under cooling to −5° C. The mixture was then stirred at −5° C. for 1 hour and at room temperature overnight. The pH of the reaction mixture was adjusted to about 6 by addition of about 50 ml of triethylamine. After 6 hours, 6 g of DCC dissolved in 10 ml of dichloromethane was added to the reaction mixture and the mixture was stirred overnight. To this, 10 ml of glacial acetic acid was added and the insoluble materials were removed by filtration and the filtrate was concentrated in vacuo. To the resultant residue, 1 liter of ethyl acetate was added and the mixture was washed with 1 N hydrochloric acid and a 5% sodium bicarbonate aqueous solution, and dried over anhydrous sodium sulfate. The ethyl acetate was removed by filtration and the residue was recrystallized twice from ethyl acetate, twice from methanol-diethyl ether to obtain 95 g of the desired material having a melting point of 111.5°-113.5° C.

(3) Production of BOC-Met-Leu-Gly-OH

BOC-Met-Leu-Gly-OBzl (10.2 g) was dissolved in 80 ml of methanol. Then, 12 ml of 2 N sodium hydroxide was added thereto under cooling with ice and the mixture was stirred at room temperature for 20 minutes. The pH of the reaction mixture was then adjusted to about 6 by addition of 1 N hydrochloric acid and the methanol was removed by evaporation. The residue was extracted with 200 ml of ethyl acetate, washed with 1 N hydrochloric acid and water, dried over anhydrous sodium sulfate and the ethyl acetate was removed by evaporation. The residue was crystallized from n-hexane and recrystallized from ethyl acetate-diethyl ether to obtain 7.8 g (yield 93%) of the desired material having a melting point of 139°-140° C.
$[\alpha]_D^{22}$ −49.6° (c=2.2, ethanol)

Elemental Analysis

Calc'd for $C_{18}H_{33}N_3O_6S_1$ (%): C 51.52, H 7.94, N 10.02; Found (%): C 51.47, H 8.13, N 10.14.

(4) Production of

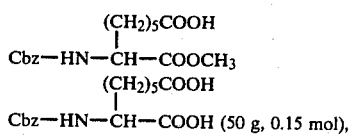

$$\text{Cbz—HN—CH—COOH} \quad (50 \text{ g, } 0.15 \text{ mol}),$$

6.9 g of paraformaldehyde, 1.5 g of p-toluenesulfonic acid and 650 ml of benzene were charged in a 1-liter eggplant type flask and heated under reflux for 3 hours.

After the reaction, the reaction mixture was allowed to cool to room temperature, the benzene solution was washed 3 times with water and dried over anhydrous sodium sulfate and the benzene was removed by evaporation in vacuo to obtain 58 g of an oily residue.

The oily residue was dissolved in 300 ml of methanolic sodium methylate solution prepared by dissolving 3.5 g of metallic sodium in 300 ml of methanol under cooling, and then the resultant mixture was allowed to stand at room temperature.

After adjusting the pH to 5 by addition of hydrochloric acid, the methanol was removed by evaporation in vacuo. The resultant oily residue was dissolved in ethyl acetate, washed with 1 N hydrochloric acid, washed 4 times with water and dried over anhydrous sodium sulfate. The ethyl acetate was removed by evaporation in vacuo to obtain 56 g of an oily material consisting of the desired material.

(5) Production of

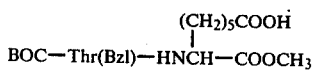

The oily material of

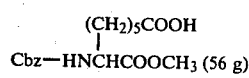

was dissolved in a solvent mixture of 300 ml of methanol and 150 ml of water and activated charcoal was added thereto. After stirring for 1 hour, palladium-carbon was added as a catalyst and hydrogenation was conducted by bubbling hydrogen gas therethrough for 10 hours. The catalyst was then removed by filtration and the filtrate was concentrated to 100 ml in vacuo. To this, 200 ml of dioxane was added and then 21 ml of triethylamine was added thereto. After addition of 80 g of BOC-Thr(Bzl)-OSU, the mixture was stirred at room temperature for 3 days. After the reaction, N,N-dimethyl-1,3-diaminopropane was added thereto and the mixture was stirred for 3 hours, and then concentrated to 100 ml in vacuo. The concentrate was extracted with ethyl acetate, and washed with 1 N hydrochloric acid and water. The ethyl acetate was removed by evaporation in vacuo and the resultant oily material was dissolved in diethyl ether, and then transferred to a 5% sodium bicarbonate aqueous solution. The aqueous layer was washed well with diethyl ether and extracted with ethyl acetate. After washing the extract with water, 1 N hydrochloric acid and water, the extract was dried over anhydrous sodium sulfate and the ethyl acetate was removed by evaporation in vacuo to obtain 57 g of an oily material consisting of the desired material.

(6) Production of

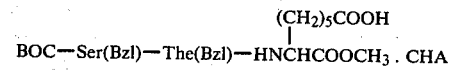

To 50 g of

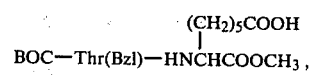

150 ml of TFA was added under cooling with ice and dissolved by shaking. The solution was allowed to stand at room temperature for 30 minutes and the TFA was removed by evaporation in vacuo. Then, the residue was dried overnight in a desiccator over sodium hydroxide.

The oily residue was dissolved in 100 ml of DMF and 40 ml of triethylamine was added thereto under cooling to adjust the pH of about 6. After addition of 5 g of HOBT and 50 g of BOC-Ser(Bzl)-OSU, the pH was adjusted again to about 6 by adding N-methylmorpholine. The resultant mixture was stirred at room temperature for 3 days and 2 ml of N,N-dimethyl-1,3-propanediamine was added thereto. The mixture is then stirred for 1 hour, water was added and the mixture was extracted with ethyl acetate. The extract was washed with 1 N hydrochloric acid, water, a 5% sodium bicarbonate aqueous solution and water and dried over anhydrous sodium sulfate.

The ethyl acetate was removed by evaporation in vacuo and the residue was dissolved in 300 ml of diethyl ether and transferred to a 5% sodium bicarbonate aqueous solution. The aqueous solution was acidified with hydrochloric acid and extracted with ethyl acetate. The extract was then washed with a 5% sodium bicarbonate aqueous solution and water, and dried over anhydrous sodium sulfate. To the ethyl acetate solution, an equal volume of cyclohexylamine was added under cooling with ice. Then the solvent was removed by evaporation in vacuo and the resultant oily residue was crystallized from diethyl ether and n-hexane to obtain 41 g of the desired material having a melting point of 70°-73° C.
$[\alpha]_D^{20}$ +49° (c=2.7, DMF)

(7) Production of BOC-Asn-Leu-OBzl

BOC-Asn-OH (26.6 g) and 43.3 g of H-Leu-OBzl·TosOH were dissolved in 150 ml of DMF and 2 g of HOBT was added thereto. To the resultant mixture, 16.3 g of WSC was added dropwise over a period of about 30 minutes while cooling at −10° C. and the mixture was stirred at room temperature overnight. Water was added to the reaction mixture to precipitate the product. The product was extracted with ethyl acetate and the extract was washed with 1 N hydrochloric acid, water, a 5% sodium carbonate aqueous solution and water, dried over anhydrous magnesium sulfate and concentrated in vacuo. The residue was recrystallized from ethyl acetate-n-hexane to obtain 44.3 g of the desired material having a melting point of 146°–147° C.

$[\alpha]_D^{25} -26.5°$ (c=2, DMF).

(8) Production of BOC-Gly-Asn-Leu-OBzl

To 15 g of BOC-Asn-Leu-OBzl, 30 ml of TFA was added while cooling with ice and the reaction was conducted at room temperature for 1 hour. The TFA was removed by evaporation in vacuo and the resultant oily residue was dried in a desiccator over sodium hydroxide and dissolved in 50 ml of DMF. The pH of the solution was adjusted to about 6.5 by addition of triethylamine under cooling with ice, 11.3 g of BOC-Gly-OSU and 1 g of HOBT were added thereto and the mixture was stirred at room temperature overnight.

After the reaction had been completed, 2 ml of N,N-dimethyl-1,3-diaminopropane was added to the reaction mixture and the mixture was stirred for 30 minutes. After addition of water, the reaction mixture was extracted twice with chloroform and the extract was washed well with 1 N hydrochloric acid and water, and dried over anhydrous magnesium sulfate. The chloroform was removed by evaporation and the resultant oily residue was crystallized from ethyl acetate-n-hexane to obtain 13.0 g (yield 76.5%) of the desired material having a melting point of 86°–88° C.

(9) Production of BOC-Gly-Asn-Leu-NHNH$_2$

BOC-Gly-Asn-Leu-OBzl (5.0 g) was dissolved in 20 ml of methanol and 20 ml of 80% hydrazine hydrate was added thereto. The mixture was allowed to stand at room temperature overnight. Diethyl ether was added to the reaction mixture to ensure complete precipitation. The precipitate was collected by filtration, washed well with diethyl ether and re-precipitated from methanol-diethyl ether to obtain 3.9 g (yield 93.7%) of the desired material having a melting point of 204°–207° C. (dec.).

(10) Production of

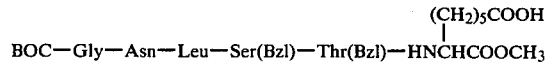

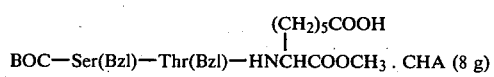

was treated with 1 N hydrochloric acid in ethyl acetate to obtain the free acid and after drying with anhydrous sodium sulfate, the mixture was concentrated in vacuo. To the resultant oily residue, 30 ml of TFA was added under cooling. The mixture was stirred at room temperature for 30 minutes and the TFA was removed by evaporation in vacuo. The residue was dried in a desiccator over sodium hydroxide and dissolved in 10 ml of DMF, and then neutralized with triethylamine.

Separately, 4.2 g of BOC-Gly-Asn-Leu-NHNH$_2$ was dissolved in 15 ml of DMF. While cooling to $-10°$ C., 3.5 ml of a 6 N hydrogen chloride dioxan solution was added thereto. Further, 2.0 ml of isoamyl nitrite was added thereto and the mixture was reacted at the same temperature for 10 minutes to azidate.

The reaction mixture containing the azide was cooled to $-50°$ C. and the DMF solution prepared as described above was added gradually thereto. After the addition, the pH was adjusted to about 7.0 with triethylamine and the mixture was stirred at a temperature ranging from $-5°$ C. to $-10°$ C. for 1 hour, and in an ice-bath overnight. After adjusting the pH to about 7.0, with N-methylmorpholine, the stirring was continued for 3 days.

the reaction mixture was added gradually to 300 ml of cold 0.5 N hydrochloric acid at $-5°$ C. while keeping the temperature at $-5°$ C. or below. The precipitate formed was collected by filtration, washed with water and heated under reflux in a solvent mixture of 100 ml of methanol and 200 ml of water for 10 minutes. After cooling, the precipitate formed was collected by filtration and heated under reflux again in a solvent mixture of 200 ml of chloroform and 100 ml of ethyl acetate. After cooling, the precipitates formed were collected by filtration and re-precipitated from methanol-diethyl ether to obtain 6.1 g (yield 63.8%) of the desired material having a melting point of 192°–194° C. (dec.).

$[\alpha]_D^{20} -6.33°$ (c=1.5, DMF)

Elemental Analysis

Calc'd for $C_{47}H_{69}O_{14}N_7 \cdot \frac{1}{2}H_2O$ (%): C 58.48, H 7.31, N 10.16; Found (%): C 58.40, H 7.30, N 10.19.

(11) Production of

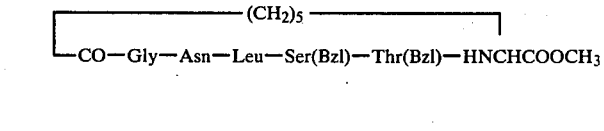

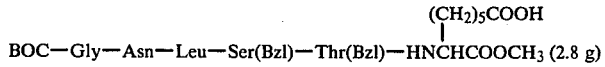

was dissolved in 30 ml of dry pyridine, 5 g of TFA-ONP was added thereto and the mixture was stirred at 45° C. for 3 hours. After the reaction, the reaction mixture was concentrated in vacuo. Diethyl ether was added to the resultant residue and the precipitate formed was collected by filtration, washed with diethyl ether and dried to obtain 2.8 g of a yellowish brown powder.

To the powder, 15 ml of TFA was added under cooling and the mixture was stirred at room temperature for 30 minutes. The TFA was removed by evaporation and the residue was dissolved in 20 ml of DMF. The solution prepared as described above was added dropwise with stirring over a period of 1 hour to 3.0 l of dry pyridine at 45° C. After the addition had been completed, the mixture was warmed to 50° C. and stirred for an additional 8 hours and overnight at 40° C. After the reaction, the reaction mixture was concentrated in vacuo to a volume of 200 ml and stirred at 40° C. for 3 hours. Then, the mixture was concentrated in vacuo again to a volume of about 50 ml and dissolved in 600 ml of chloroform. The resultant mixture was washed with a saturated sodium chloride aqueous solution, twice with 1 N hydrochloric acid, and with a sodium chloride aqueous solution. The chloroform layer was concentrated in vacuo to a volume of about 10 ml. Diethyl ether was added thereto and the precipitate formed was collected by filtration, washed with diethyl ether and dried to obtain 1.5 g (yield 60%) of the desired material.

(12) Production of

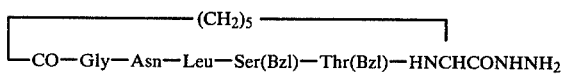

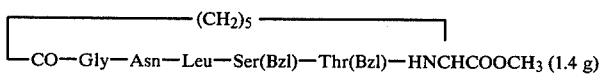

was dissolved in a solvent mixture of 5 ml of DMF and 30 ml of methanol. After the addition of 20 ml of 80% hydrazine hydrate, the mixture was stirred at room temperature overnight. After the reaction, water was added to the reaction mixture and the precipitate formed was collected by filtration and washed with water. The precipitate was dissolved in a solvent mixture of 50 ml of methanol and 50 ml of ethyl acetate and heated under reflux. After cooling, the precipitate formed was collected by filtration and dried to obtain 1.1 g (yield 78.6%) of the desired material having a melting point of 212 (softened)-236°-250° C. (dec.).

$[\alpha]_D^{25} - 15.5°$ (c=0.2, DMF).

(13) Production of

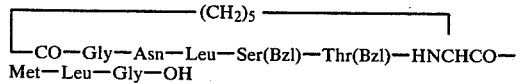

To 2 g of BOC-Met-Leu-Gly-OH prepared as described in (3) above, 0.5 ml of dimethyl thioether and 10 ml of TFA was added under cooling. After stirring at room temperature for 20 minutes, the TFA was removed by evaporation in vacuo. Diethyl ether was added to the resultant residue, and the precipitate was collected by decantation, dried in a desiccator over sodium hydroxide and dissolved in 2 ml of DMF.

Separately, 840 mg of

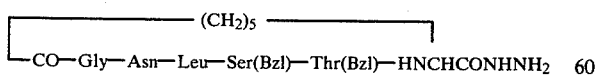

was suspended in 5 ml of DMF. While cooling at −5° C., 1 ml of dioxane containing 6 N hydrogen chloride was added thereto and the hexapeptide was dissolved completely by increasing the temperature to 10° C. The solution was then cooled to −5° C. or below, 0.2 ml of isoamyl nitrite was added thereto gradually and the reaction was carried out at the same temperature for 10 minutes to azidate. After the azidation had been completed, the reaction mixture was cooled to −50° C. and the DMF solution prepared as described above was added gradually thereto. Then, the mixture was neutralized with triethylamine and stirred at −5° C. for 1 hour and reacted at 0° C. for 3 days additionally.

The reaction mixture was added gradually to 200 ml of 0.5 N hydrochloric acid under cooling and the precipitate formed was collected by filtration. The precipitate was washed with water and refluxed in 200 ml of methanol. After cooling to room temperature, the resultant precipitate was collected by filtration and 1.1 g of the desired material having a melting point of 243°-247° C. (dec.) was obtained.

$[\alpha]_D^{25} - 10.7°$ (c=0.31, DMF)

Elemental Analysis

Calc'd for $C_{54}H_{80}N_{10}O_{14}S \cdot 3/2H_2O$ (%): C 56.27, H 7.27, N 12.15; Found (%): C 56.17, H 7.07, N 12.29.

Amino Acid Analysis

Asp 0.96(1), Thr 0.94(1), Ser 0.88(1), Gly 2.00(2), Met 0.99(1), Leu 1.88(2), α-aminosuberic acid 1.02(1), NH3 1.08; (II-B) Production of Docosapeptide Fragment of the Formula BOC-Thr(Bzl)-Tyr[Bzl(Cl₂)]-Thr(Bzl)-Gln-Asp(OBzl)-Phe-Asn-Lys[Cbz(o-Cl)]-Phe-His-Thr(Bzl)-Phe-Pro-Gln-Thr(Bzl)-Ala-Ile-Gly-Val-Gly-Ala-Pro-NH₂ (amino acid sequence 10-31).

(1) Production of Cbz-Ala-Pro-NH₂

Cbz-Ala-OH (74.1 g), 50 g of H-Pro-NH₂·HCl and 50.5 g of HOBT were dissolved in 300 ml of DMF and the solution was cooled to 0° to 3° C. To the solution, 61 ml of WSC was added and the solution was stirred at the same temperature for about 1 hour and at room temperature overnight. The solvent was then removed by evaporation and the residue was dissolved in chloroform, washed with 1 N hydrochloric acid, water, a 5% sodium bicarbonate aqueous solution and water, and dried over magnesium sulfate. The mixture was concentrated in vacuo, the resulting residue was treated with diethyl ether, and the insoluble material was collected by filtration and recrystallized twice from ethanol to obtain 71 g (yield: 67.6%) of the desired material having a melting point of 171.3°-171.8° C.

$[\alpha]_D^{19} - 94.2°$ (c=2, methanol)

(2) Production of BOC-Val-Gly-OEt 1 liter of ethyl acetate was added to 80 g of BOC-Val.DCHA and the mixture was washed twice with 600 ml of sulfuric acid and water, dried over anhydrous sodium sulfate and concentrated in vacuo to obtain the free acid in an oily form. The free acid and 28 g of H-Gly-OEt.HCl were dissolved in a solvent mixture of 150 ml of chloroform and 150 ml of THF. The solution was cooled and 28 ml of triethylamine and 41.2 g of DCC were added thereto. The resultant mixture was stirred at a temperature of 0° to −2° C. for 1 hour and at room temperature overnight. The insoluble materials were removed by filtration and the filtrate was concentrated in vacuo. The residue was dissolved in ethyl acetate, washed with 1 N hydrochloric acid, water, a 5% sodium bicarbonate aqueous solution and water, dried over magnesium sulfate and concentrated in vacuo. The resulting residue was crystallized by addition of n-hexane and recrystallized from ethyl acetate-diethyl ether-n-hexane to obtain 54 g (89.2%) of the desired material with a melting point of 94°–96° C.

(3) Production of BOC-Val-Gly-OH

BOC-Val-Gly-OEt (10 g) was dissolved in 20 ml of methanol and 40 ml of 1 M sodium hydroxide was added thereto under cooling. The mixture was stirred with cooling for 15 minutes and at room temperature for an additional 45 minutes. The pH of the reaction mixture was adjusted to a pH of about 7 with 1 N hydrochloric acid and concentrated in vacuo. Water was then added to the residue and the mixture was washed with diethyl ether. The pH of the water layer was adjusted to a pH of about 2 with 1 N hydrochloric acid and the layer was extracted with ethyl acetate. The ethyl acetate layer was washed well with water, dried over magnesium sulfate and concentrated in vacuo. The resultant oily residue was solidified by addition of n-hexane and recrystallized from ethyl acetate-n-hexane to obtain 8.0 g (yield: 89%) of the desired material having a melting point of 101°–104° C.

(4) Production of BOC-Val-Gly-Ala-Pro-NH$_2$

Cbz-Ala-Pro-NH$_2$ (30 g) was dissolved in 200 ml of a 25% hydrogen bromide acetic acid solution and stirred at room temperature for 30 minutes. After the reaction, diethyl ether was added and the precipitate formed was collected by filtration, washed well with diethyl ether and dried in a desiccator over sodium hydroxide. The material was then dissolved in 200 ml of DMF and 26 g of BOC-Val-Gly-OH and 12.8 g of HOBT were added thereto. After addition of 17.4 ml of WSC under cooling with ice, the mixture was stirred at the same temperature for about 1 hour. The pH of the reaction mixture was adjusted to a pH of about 4 by addition of about 5 ml of N-methylmorpholine and the mixture was stirred at room temperature overnight. The DMF was removed by evaporation and water was added to the residue. After saturation with sodium chloride, the mixture was extracted with chloroform and the chloroform layer was washed with 1 N hydrochloric acid saturated with sodium chloride, water and a 5% sodium bicarbonate aqueous solution, dried over magnesium sulfate and concentrated in vacuo. The residue was recrystallized from ethanol to obtain 36 g (yield: 85.9%) of the desired material having a melting point of 201°–202° C.

$[\alpha]_D^{30} - 79.9°$ (c=1.0, acetic acid)

(5) Production of BOC-Ile-Gly-OEt

To 120 g of BOC-Ile-OH·½H$_2$O, 200 ml of chloroform and 200 ml of toluene were added and the mixture was concentrated in vacuo. The resultant oily residue was dissolved in 300 ml of dichloromethane and 77 g of H-Gly-OEt-·HCl was added thereto. The mixture was stirred under cooling and neutralized with triethylamine then 200 ml of chloroform was added thereto. To the resultant mixture, 114 g of DCC dissolved in 100 ml of chloroform was added dropwise over a period of 1 hour and the mixture was stirred at room temperature for 18 hours. After addition of 4 ml of acetic acid, the mixture was stirred for 2 hours additionally and the insoluble material was removed by filtration. The filtrate was washed with chloroform and concentrated in vacuo. After addition of chloroform, the residue was washed with water, 1 N hydrochloric acid, water, a 5% sodium bicarbonate aqueous solution and water. The mixture was then dried over magnesium sulfate, concentrated in vacuo, and the residue was crystallized from diethyl ether-n-hexane and recrystallized from hot ethyl acetate-diethyl ether-n-hexane to obtain 126.1 g of the desired material having a melting point of 107°–108° C.

$[\alpha]_D^{19} - 12.6°$ (c=1, DMF)

(6) Production of BOC-Ala-Ile-Gly-OEt

To 8.0 g of BOC-Ile-Gly-OEt, 20 ml of TFA was added at −5° C. and the mixture was reacted for 40 minutes. After removal of the TFA by evaporation, diethyl ether was added to the residue. The precipitate was collected by decantation and dried in a desiccator over sodium hydroxide. The precipitate was dissolved in 40 ml of DMF, neutralized with triethylamine and reacted with 8.7 g of BOC-Ala-ONSU for 2 days. Following this, 2 ml of N,N-dimethyl-1,3-diaminopropane was added to the reaction mixture and the mixture was reacted for 1 hour. The DMF was removed by evaporation in vacuo, chloroform was then added to the resultant residue and the mixture was washed with water, 1 N hydrochloric acid, water, a 5% sodium carbonate aqueous solution and water. Then, the mixture was dried over magnesium sulfate and concentrated in vacuo. The residue was recrystallized from ethyl acetate to obtain 8.8 g (yield: 84.9%) of the desired material with a melting point of 190°–190.5° C.

$[\alpha]_D^{17} - 26.7°$ (c=1, DMF)

(7) Production of BOC-Ala-Ile-Gly-OH

BOC-Ala-Ile-Gly-OEt (8.5 g) was dissolved in 70 ml of methanol and 25 ml of a 1 N sodium hydroxide aqueous solution was added dropwise thereto while cooling at −5° C. After stirring for 5 hours, the pH was adjusted to a pH of about 4 to 5 with 1 N hydrochloric acid and the methanol was removed by concentration in vacuo. After addition of water, the pH of the mixture was adjusted to a pH of about 7 with 1 N hydrochloric acid and the mixture was extracted twice with ethyl acetate. The ethyl acetate layer was dried over magnesium sulfate and concentrated and the residue was recrystallized three times from ethyl acetate to obtain 6.8 g (yield: 84.8%) of the desired material having a melting point of 205.6°–207.5° C.

$[\alpha]_D^{17} - 34.7°$ (c=0.7, DMF)

(8) Production of BOC-Gln-Thr(Bzl)-OBzl

H-Thr(Bzl)-OBzl(COOH)$_2$ (21.4 g) was suspended in 300 ml of ethyl acetate and 100 ml of a 1 M sodium carbonate aqueous solution was added thereto. The resultant mixture was shaken sufficiently and after the insoluble materials were removed by filtration, the ethyl acetate layer was separated. This layer was washed with a saturated sodium chloride aqueous solution, dried over sodium sulfate and concentrated in vacuo. The resultant oily residue was dissolved in 40 ml of THF and 12.3 g of BOC-Gln-OH and 6.8 g of HOBT were dissolved therein. After dropwise addition of 10.3 g of DCC dissolved in 10 ml of THF over a period of 5 minutes under cooling, the mixture was stirred at the same temperature for 21 hours additionally. The insoluble materials collected by filtration were washed with THF and the filtrate and washings were combined and concentrated in vacuo. The resultant oily residue was dissolved in ethyl acetate then allowed to stand in the cold for 1 hour. The insoluble materials precipitated were removed by filtration and the ethyl acetate layer was washed with water, 1 N hydrochloric acid, water, a 5% sodium bicarbonate aqueous solution (three times), water, 1 N hydrochloric acid (three times) and a sodium chloride aqueous solution (three times). This organic layer was then dried over magnesium sulfate and concentrated in vacuo. The residue was crystallized by addition of a small quantity of n-hexane and a large quantity of diethyl ether and the crystals were collected by filtration and recrystallized from ethyl acetate-diethyl ether to obtain 22.3 g (yield: 84.5%) of the desired material having a melting point of 88°–89.5° C.

$[\alpha]_D^{30} - 25.1°$ (c=1.1, methanol)

(9) Production of BOC-Gln-Thr(Bzl)-NHNH$_2$

BOC-Gln-Thr(Bzl)-OBzl (16.4 g) was dissolved in 20 ml of methanol and after addition of 20 g of 80% hydrazine hydrate, the mixture was stirred for 44 hours. After the reaction, water was added to the mixture and the crystals were comminuted and collected by filtration. The crystals were washed with water and diethyl ether, and recrystallized from hot methanoldiethyl ether to obtain 8.2 g (yield: 58.5%) of the desired material.

$[\alpha]_D^{30} - 9.9°$ (c=1.0, methanol)

Elemental Analysis

Calc'd for $C_{21}H_{33}O_6N_5$ (%): C 55.89, H 7.52, N 15.17; Found (%): C 55.86, H 7.37, N 15.51.

(10) Production of BOC-Gln-Thr(Bzl)-Ala-Ile-Gly-OH

To 3.6 g of BOC-Ala-Ile-Gly-OH, 15 ml of TFA was added while cooling at −5° C. and then the mixture was reacted at room temperature for 40 minutes. After removal of the TFA by evaporation, diethyl ether was added to the residue. The precipitate was dissolved in 30 ml of water, neutralized with a 1 M sodium bicarbonate aqueous solution and concentrated in vacuo. The residue was dissolved again in 10 ml of water and 1.4 ml of triethylamine was added thereto. After addition of 10 ml of DMF under cooling, the mixture was cooled to −15° C.

Separately, 5.87 g of BOC-Gln-Thr(Bzl)-NHNH$_2$ was dissolved in 40 ml of DMF and the solution was cooled to −20° C. To this solution, 9 ml of a 6 N hydrogen chloride dioxane solution was added dropwise. After gradual addition of 2.28 ml of isoamyl nitrite at −15° C., the mixture was stirred at −10° C. for 50 minutes. The mixture was then cooled to −20° C. and 7.56 ml of triethylamine was gradually added thereto.

The cold DMF solution prepared as described above was added to the resultant mixture. The mixture was stirred at −10° C. for 1.5 hours and the reaction was kept in an ice bath for 6 days.

Following this, 200 ml of 1% acetic acid was added to the reaction mixture and the precipitate formed was collected by filtration, washed with water and diethyl ether, and reprecipitated from methanol-diethyl ether to obtain 3.3 g (yield: 48.7%) of the desired material having a melting point of 230°–232° C. (dec.).

$[\alpha]_D^{23} - 32.7°$ (c=1.0, acetic acid)

(11) Production of BOC-Gln-Thr(Bzl)-Ala-Ile-Gly-Val-Gly-Ala-Pro-NH$_2$

To 2.65 g of BOC-Val-Gly-Ala-Pro-NH$_2$, 10 ml of TFA was added and the mixture was reacted for 50 minutes. After removal of the TFA by evaporation in vacuo, diethyl ether was added to the resultant residue and the precipitate was collected by decantation and dried in a desiccator over sodium hydroxide. This material was then dissolved in a solvent mixture of 20 ml of DMF and 20 ml of HMPA, and 3.87 g of BOC-Gln-Thr(Bzl)-Ala-Ile-Gly-OH and 0.82 g of HOBT were added with stirring and dissolved therein. The resultant solution was cooled to below 0° C. and, after addition of 1.1 ml of WSC, the mixture was stirred at the same temperature and reacted. After reaction for 3 days, 200 ml of 2% acetic acid was added to the reaction mixture and the precipitate formed was collected by filtration and washed with water and diethyl ether. The precipitate was heated under reflux with methanol and then allowed to cool to precipitate. Further, 50 ml of ethyl acetate and 50 ml of diethyl ether were added thereto and the mixture was allowed to cool. The precipitate formed was collected by filtration, washed with ethyl acetate to obtain 4.1 g (yield: 71.8%) of the desired material having a melting point of 250°–260° C. (dec.).

$[\alpha]_D^{28} - 57.0°$ (c=1.0, acetic acid)

Elemental Analysis

Calc'd for $C_{47}H_{75}O_{13}N_{11} \cdot 3/2H_2O$ (%): C 54.85, H 7.64, N 14.97; Found (%): C 55.18, H 7.60, N 14.54.

(12) Production of Cbz-Phe-His-OMe

H-His-OMe·2HCl (126 g) and 213 g of Cbz-Phe-ONSU were suspended in 600 ml of chloroform and stirred under cooling. To the mixture, 145.6 ml of triethylamine was added dropwise over a period of about 40 minutes then the mixture was stirred at room temperature for 4 days. After addition of 1 liter of chloroform, the mixture was washed with a 5% sodium carbonate aqueous solution (twice), water (4 times) and a saturated sodium chloride aqueous solution (twice), dried over magnesium sulfate and concentrated in vacuo. To the resultant residue, a solvent mixture of diethyl ether and n-hexane (1:2 by volume) was added and the crystals formed were collected by filtration and washed with the same solvent mixture. The crystals were recrystallized from methanol-ethyl acetate and after addition of diethyl ether, the crystals were collected by filtration and washed with diethyl ether to obtain 216.5 g (yield: 92.5%) of the desired material having a melting point of 135°–140° C.

(13) Production of BOC-Lys[Cbz(o-CL)]-Phe-His-OMe

To 27 g of Cbz-Phe-His-OMe, 110 ml of a 26% hydrogen bromide acetic acid solution was added under cooling. The mixture was stirred and the temperature was increased to room temperature after 5 minutes, then the stirring was continued for an additional 60 minutes. Following this, dry diethyl ether was added to the mixture and the precipitate formed was washed three times by decantation, collected by filtration and dried in a desiccator over sodium hydroxide.

The HBr salt obtained was dissolved in 100 ml of DMF and neutralized with 16.8 ml of triethylamine under cooling. To the solution, 32.2 g of BOC-Lys[Cbz(o-Cl)]-ONP was added and the resultant mixture was stirred for 30 minutes under cooling and at room temperature for 70 hours. The reaction mixture was then concentrated to dryness in vacuo and 350 ml of ethyl acetate and 150 ml of water were added to the residue. After adjusting the pH of the aqueous layer to a pH of 8–9 by addition of a sodium carbonate aqueous solution, the aqueous layer was separated. The ethyl acetate layer was washed 5 times with 150 ml of a 5% sodium bicarbonate aqueous solution and twice with 150 ml of a saturated sodium chloride aqueous solution, dried over magnesium sulfate and concentrated in vacuo. The crystalline residue, after addition of diethyl ether, was collected by filtration and recrystallized from 700 ml of ethyl acetate and 50 ml of methanol. The crystals were washed with ethyl acetate to obtain 27.5 g (yield: 64.2%) of the desired material having a melting point of 134°–136° C.

$[\alpha]_D^{32} - 19.8°$ (c=1.0, DMF)

Elemental Analysis

Calc'd for $C_{35}H_{45}O_8N_6Cl \cdot \frac{1}{2}H_2O$ (%): C 58.20, H 6.42, N 11.69; Found (%): C 58.36, H 6.48, N 11.64.

(14) Production of BOC-Asn-Lys[Cbz(o-Cl)]-Phe-His-OMe

BOC-Lys[Cbz(o-Cl)]-Phe-His-OMe (27.1 g) was treated with 60 ml of TFA under cooling for 10 minutes and at room temperature for 65 minutes. After concentration in vacuo, diethyl ether was added to the resultant oily residue. The precipitate formed was collected by decantation and dried in a desiccator over sodium hydroxide. This material was then dissolved in 50 ml of DMF, neutralized with triethylamine and 16.1 g of BOC-Asn-ONP was added thereto. The mixture was stirred under cooling for 1 hour and at room temperature for 72 hours. After the reaction, the reaction mixture was concentrated in vacuo and water was then added to the residue. After adjusting the pH of a pH of 9 by addition of a saturated sodium carbonate aqueous solution, the precipitate was collected by filtration, washed with water and diethyl ether, and dried. The precipitate was re-precipitated from methanol-ethyl acetate then from methanol-diethyl ether to obtain 15.6 g (yield: 49%) of the desired material having a melting point of 175°–176° C.

$[\alpha]_D^{32} - 44.2°$ (c=1.0, DMF)

Elemental Analysis

Calc'd for $C_{39}H_{51}O_{10}N_8Cl \cdot 4/3H_2O$ (%): C 55.02, H 6.35, N 13.16; Found (%): C 55.22, H 6.14, N 12.79.

(15) Production of BOC-Asn-Lys[Cbz(o-Cl)]-Phe-His-NHNH₂

BOC-Asn-Lys[Cbz(o-Cl)]-Phe-His-OMe (8.3 g) was dissolved in a solvent mixture of 20 ml of methanol and 10 ml of DMF. After addition of 6.3 ml of 80% hydrazine hydrate, the resulting mixture was stirred. After reaction for 5 days, water was added to the reaction mixture and the crystals formed were collected by filtration and washed with water. The crystals were heated under reflux in 150 ml of methanol and allowed to cool. After addition of 200 ml of diethyl ether, the mixture was allowed to stand and the precipitate was collected by filtration and washed with diethyl ether to obtain 6.9 g (yield: 84.5%) of the desired material having a melting point of 200°–202° C. (dec.).

$[\alpha]_D^{26} - 43.0°$ (c=1.1, DMF)

Elemental Analysis

Calc'd for $C_{38}H_{51}O_9N_{10}Cl \cdot \frac{1}{2}H_2O$ (%): C 54.57, H 6.27, N 16.75; Found (%): C 54.36, H 6.28, N 16.90.

(16) Production of BOC-Phe-Pro-OBzl

To 121 g of H-Pro-OBzl·HCl, 400 ml of THF was added and 70 ml of triethylamine was added dropwise thereto under cooling with stirring. Further, 100 ml of THF and 50 ml of chloroform were added thereto. To the resultant mixture, 132 g of BOC-Phe-OH was added and 113 g of DCC dissolved in 100 ml of chloroform was added dropwise under cooling with stirring over a period of 1 hour. The mixture was stirred at a temperature below 10° C. and after 16 hours, 5 ml of acetic acid was added thereto under cooling. After stirring for an additional 2 hours, the insoluble materials were removed by filtration and the filtrate was washed with THF and concentrated in vacuo. The resultant oily residue was dissolved in 1 liter of ethyl acetate and the insoluble materials were removed by filtration. The filtrate was washed with water, 1 N hydrochloric acid, water, a 5% sodium bicarbonate aqueous solution and water, dried over magnesium sulfate and concentrated in vacuo. The resultant oily residue was dissolved in diethyl ether and crystallized by addition of n-hexane. The crystals were recrystallized from ethyl acetate-n-hexane to obtain 169 g (yield: 74.8%) of the desired material having a melting point of 104°–106° C.

(17) Production of BOC-Thr(Bzl)-Phe-Pro-OBzl

To 67.9 g of BOC-Phe-Pro-OBzl, 150 ml of TFA was added under cooling. After stirring for 40 minutes, the mixture was concentrated again. The resultant oily residue was dried in a desiccator over sodium hydroxide. This material was then dissolved in 140 ml of DMF and, after neutralization with triethylamine under cooling, 67.1 g of BOC-Thr(Bzl)-ONSU was added thereto. The mixture was stirred under cooling for 1 hour and then at room temperature. During this time, the pH of the reaction mixture was adjusted to a pH of about 7 by addition of triethylamine. After 72 hours, N-methylmorpholine was added to the mixture and the reaction was continued at 25° C. After reaction for 117 hours, 2 ml of N,N-dimethyl-1,3-diaminopropane was added and the mixture was stirred for 2 hours and then concentrated in vacuo. Water and chloroform were added to the residue and the chloroform layer was separated, washed with water, 1 N hydrochloric acid, water, a 10% sodium carbonate aqueous solution and water, and dried over magnesium sulfate. The layer was concentrated in vacuo and the resultant residue was crystallized from methanoldiethyl ether. The crystals were collected by filtration, washed with methanol and recrystallized from methanol to obtain 64 g (yield: 66.3%) of the desired material having a melting point of 132°–133° C.

$[\alpha]_D^{30} - 29.0°$ (c=1.0, DMF)

(18) Production of BOC-Thr(Bzl)-Phe-Pro-OH·CHA

BOC-Thr(Bzl)-Phe-Pro-OBzl (64.4 g) was dissolved in 200 ml of THF, and 120 ml of 1 N sodium hydroxide was added dropwise thereto under cooling with stirring over a period of 30 minutes. Further, 50 ml of THF and 50 ml of methanol were added thereto and the mixture was stirred at room temperature for 3.5 hours. After the reaction, the pH of the reaction mixture was adjusted to a pH of 7 by addition of 25 ml of 1 N hydrochloric acid and the mixture was concentrated in vacuo. Water was added to the residue, and further 800 ml of chloroform and 110 ml of 1 N hydrochloric acid were added to adjust the pH to 2–3. The chloroform layer was separated and washed twice with water, dried over sodium sulfate and concentrated in vacuo.

The resultant oily residue was dissolved in ethyl acetate and the solution was concentrated in vacuo. The residue was dissolved again in diethyl ether. To the solution, 12 ml of cyclohexylamine was added to form crystals and the crystals were collected by filtration, and washed with diethyl ether to obtain 58.9 g (yield: 90.3%) of the desired material having a melting point of 90°–115° C.

$[\alpha]_D^{30} -20.2°$ (c=1.0, DMF)

(19) Production of BOC-Asn-Lys[Cbz(o-Cl)]-Phe-His-Thr(Bzl)-Phe-Pro-OH

BOC-Thr(Bzl)-Phe-Pro-OH·CHA (46 g) was shaken with a solvent mixture of 200 ml of 1 N hydrochloric acid and 500 ml of ethyl acetate. The aqueous layer was extracted with 150 ml of ethyl acetate and the ethyl acetate layers were combined and washed with 0.5 N hydrochloric acid and water, dried over magnesium sulfate and concentrated in vacuo. To the resultant oily residue, 100 ml of TFA was added under cooling and the mixture was stirred for 1 hour and 40 minutes and then concentrated to dryness in vacuo. The residue was crystallized by addition of diethyl ether and the crystals were collected by filtration, washed with diethyl ether and dried in a desiccator over sodium hydroxide in vacuo. This material was then dissolved in 100 ml of DMF and cooled to −20° C.

Separately, 250 ml of DMF was added to 57 g of BOC-Asn-Lys[Cbz(o-Cl)]-Phe-His-NHNH$_2$. After the mixture was cooled to −20° C., 46 ml of a 6 N hydrogen chloride dioxane solution was added dropwise thereto. Further, 12.04 ml of isoamyl nitrite was added dropwise to the mixture at a temperature of −15° C. to −10° C. The mixture was stirred at −10° C. for 40 minutes and then cooled again to −20° C. The DMF solution prepared as described above was added to this mixture. To the resultant mixture, 58.2 ml of triethylamine was added dropwise at a temperature of −20° C. to −15° C. After reaction at −5° to 0° C. for 4 days, the mixture was concentrated in vacuo. To the residue, 500 ml of ethyl acetate was added and the precipitate formed was collected by filtration, dried, washed with water and diethyl ether, dried and then washed with ethyl acetate, and diethyl ether. The precipitate was heated in ethyl acetate under reflux and after cooling, the precipitate was collected by filtration and recrystallized from methanol-diethyl ether to obtain 78 g (yield: 90.7%) of the desired material having a melting point of 150°–155° C. (dec.).

$[\alpha]_D^{27} -32.1°$ (c=1.0, DMF)

Elemental Analysis

Calc'd for $C_{63}H_{78}O_{14}N_{11}Cl \cdot 2H_2O$ (%): C 58.89, H 6.43, N 11.99; Found (%): C 58.35, H 6.12, N 12.31.

(20) Production of BOC-Asn-Lys[Cbz(o-Cl)]-Phe-His-Thr(Bzl)-Phe-Pro-Gln-Thr(Bzl)-Ala-Ile-Gly-Ala-Pro-NH$_2$ BOC-Gln-Thr(Bzl)-Ala-Ile-Gly-Val-Pro-NH$_2$ (3.9 g) was treated with 10 ml of TFA and reacted under cooling for 5 minutes and at room temperature for 40 minutes. The mixture was concentrated to dryness in vacuo. After addition of 0.65 ml of 6 N hydrogen chloride dioxane solution, diethyl ether was added thereto to form a precipitate. The precipitate was washed twice with diethyl ether by decantation and dried in a desiccator over sodium hydroxide in vacuo. The material was dissolved in a solvent mixture of 10 ml of DMF and 15 ml of HMPA, and further 545 mg of HOBT and 5.0 g of BOC-Asn-Lys-[Cbz(o-Cl)]-Phe-His-Thr(Bzl)-Phe-Pro-OH were added and dissolved. The resultant mixture was cooled to below 0° C. with stirring and 0.75 ml of WSC was added thereto. After reaction for 24 hours, the mixture was concentrated in vacuo. To the residue, 500 ml of ethyl acetate was added and the precipitate formed was collected by filtration, washed with ethyl acetate and diethyl ether. The crystals collected by filtration were comminuted in water and the pH was adjusted to a pH of 9 by addition of a sodium carbonate aqueous solution and the precipitate was collected, washed with water and diethyl ether, then heated in 100 m of methanol under reflux. After cooling, diethyl ether was added and the crystals formed were collected by filtration and washed with methanol to obtain 7.1 g (yield: 85.3%) of the desired material having a melting point of 228°–231° C. (dec.).

$[\alpha]_D^{27} -43.2°$ (c=1.0, acetic acid)

Elemental Analysis

Calc'd for $C_{105}H_{143}O_{24}N_{22}Cl \cdot 3/2H_2O$ (%): C 58.39, H 6.81, N 14.27; Found (%): C 58.34, H 6.87, N 14.35.

Amino Acid Analysis

Lys 0.90(1), His 0.99(1), Asp 0.99(1), Thr 1.72(2), Glu 1.11(1), Pro 2.18(2), Gly 2.00(2), Ala 2.04(2), Val 1.02(1), Ile 1.13(1), Phe 2.12(2)

(21) Production of BOC-Asp(OBzl)-Phe-OH

In 10 ml of DMF, 3.3 g of phenylalanine was suspended, 2.8 ml of triethylamine was added thereto and the mixture was stirred. After addition of 4 ml of water, 8.9 g of BOC-Asp(OBzl)-ONP was added and the mixture was stirred. After 44 hours, 4.4 g of BOC-Asp(OBzl)-ONP was additionally added thereto and the reaction was continued for 3 days. The reaction mixture was concentrated in vacuo, and water and 1 N hydrochloric acid were added to adjust the pH to 2. The mixture was extracted with ethyl acetate and the ethyl acetate layer was washed with 1 N hydrochloric acid, water and a sodium chloride aqueous solution, dried over sodium sulfate, and concentrated in vacuo. The resultant oily residue was dissolved in diethyl ether and concentrated to form crystals. The crystals were collected by filtration, washed with diethyl ether and recrystallized from ethyl acetate-diethyl ether-n-hexane to obtain 3.7 g of the desired material having a melting point of 146°–147° C.

$[\alpha]_D^{20} +3.9°$ (c=1.0, methanol)

(22) Production of BOC-Gln-Asp(OBzl)-Phe-OH

BOC-Asp(OBxl)-Phe-OH (3.3 g) was reacted with 10 ml of TFA under cooling for 20 minutes and at room temperature for 40 minutes. After the reaction, the mixture was concentrated to dryness and diethyl ether was added to the residue to form crystals. The crystals were collected by filtration, washed with diethyl ether and dried in a desiccator over sodium hydroxide in vacuo. The material was then dissolved in 10 ml of DMF and 1.96 ml of triethylamine was added thereto under cooling with stirring to neutralize. Then, 3.34 g of BOC-Gln-ONP was added and the mixture was stirred for 42 hours. After the reaction, the DMF was removed by evaporation and ethyl acetate and 1 N hydrochloric acid were added to the residue. The aqueous layer was extracted again with ethyl acetate and the ethyl acetate layers were combined and washed with 1 N hydrochloric acid and water. The crystals formed by addition of diethyl ether to the ethyl acetate layers were collected by filtration. The crystals were comminuted in 0.5 N hydrochloric acid and collected by filtration. The crystals were recrystallized from methanol-diethyl ether to obtain 3.5 g (yield: 83.5%) of the desired material having a melting point of 161°–163° C. (dec.).

$[\alpha]_D^{26} -17.0°$ (c=1.1, DMF)

Elemental Analysis

Calc'd for $C_{30}H_{38}O_9N_4 \cdot H_2O$ (%): C 58.43, H 6.54, N 9.09; Found (%): C 58.03, H 6.23, N 9.37.

Production of BOC-Thr(Bzl)-Gln-Asp(OBzl)-Phe-OH

To 45 g of BOC-Gln-Asp(OBzl)-Phe-OH, 100 ml of TFA was added under cooling. After stirring for 50 minutes, the reaction mixture was concentrated in vacuo. Dry diethyl ether was added to the residue and the precipitate formed was collected by filtration, washed with diethyl ether and dried in a desiccator over sodium hydroxide in vacuo. To the powder, 200 ml of DMF was added and 200 ml of a solvent mixture of DMF and water (1:1 by volume) was added thereto under cooling with stirring. Then, 21 ml of triethylamine was added dropwise to the solution. After addition of 33.7 g of BOC-Thr(Bzl)-ONSU, the resultant mixture was stirred and reacted. After reaction for 20 hours, 5 ml of N-methylmorpholine was added and the reaction was continued for 22 hours. The reaction mixture was then concentrated in vacuo and the resultant oily residue was crystallized by addition of 1 liter of 1 N hydrochloric acid. The crystals were comminuted in a mortar and collected by filtration, washed with water and diethyl ether and recrystallized from methanol-diethyl ether to obtain 46.5 g (yield: 78.5%) of the desired material having a melting point of 172°–173.5° C. (dec.).

$[\alpha]_D^{26} -3.7°$ (c=1.0, DMF)

Elemental Analysis

Cald'd for $C_{41}H_{51}O_{11}N_5 \cdot 1/2H_2O$ (%): C 61.64, H 6.56, N 8.77; Found (%): C 61.61, H 6.57, N 9.00.

(24) Production of BOC-Tyr[Bzl(Cl₂)]-Thr(Bzl)-Gln-Asp(OBzl)-Phe-OH

To 45 g of BOC-Thr(Bzl)-Gln-Asp(OBzl)-Phe-OH, 100 ml of TFA was added under cooling. The mixture was stirred under cooling for 10 minutes and at room temperature for 60 minutes and then concentrated to dryness in vacuo. The residue was crystallized by addition of diethyl ether and the crystals were collected by filtration, washed with diethyl ether and dried in a desiccator over sodium hydroxide in vacuo.

The powder was dissolved in 100 ml of DMF and the solution was neutralized by addition of triethylamine under cooling with stirring. To the solution, 32.2 g of BOC-Tyr-[Bzl(Cl₂)]-ONSU was added and the mixture was stirred under cooling for 1 hour and at room temperature for 46 hours. The reaction mixture was then concentrated in vacuo and the residue was crystallized by addition of cold 0.5 B hydrochloric acid under cooling. The crystals were comminuted and collected by filtration and washed with water, diethyl ether and ethyl acetate. The crystals were heated in a solvent mixture of 150 ml of methanol and 150 ml of ethyl acetate under reflux. After cooling, diethyl ether was added to the reaction mixture and the precipitate formed was collected by filtration and washed with diethyl ether to obtain 54.5 g (yield: 86%) of the desired material having a melting point of 198°–199° C. (dec.).

$[\alpha]_D^{28} +0.9°$ (c=1.0, DMF)

Elemental Analysis

Calc'd for $C_{57}H_{64}O_{13}N_6Cl_2 \cdot \frac{1}{2}H_2O$ (%): C 61.07, H 5.84, N 7.50; Found (%): C 60.92, H 5.78, N 7.85.

(25) Production of BOC-Thr(Bzl)-Tyr[Bzl(Cl₂)]-Thr(Bzl)-Gln-Asp(OBzl)-Phe-OH

To 51 g of BOC-Tyr[Bzl(Cl₂)]-Thr(Bzl)-Gln-Asp(OBzl)-Phe-OH, 130 ml of TFA was added and the mixture was stirred under cooling for 5 minutes and at room temperature for 50 minutes and then concentrated to dryness in vacuo. Diethyl ether was added to the residue and the precipitate was collected by filtration, washed with diethyl ether and dried in a desiccator over sodium hydroxide in vacuo. The powder was dissolved in 120 ml of DMF and the solution was neutralized with triethylamine under cooling with stirring. After addition of 19.6 g of BOC-Thr(Bzl)-ONSU, the mixture was stirred at room temperature. After 20 hours, the pH of the reaction mixture was adjusted to a pH of 7–8 by addition of triethylamine and then the reaction was continued for an additional 20 hours. The mixture was concentrated in vacuo and the residue was crystallized by addition of 1 liter of cold 0.5 B hydrochloric acid under cooling. The crystals were comminuted and collected by filtration and washed with water and diethyl ether. The crystals were then heated in 200 ml of methanol under reflux for 20 minutes. After addition of 100 ml of ethyl acetate, the mixture was allowed to cool and further 600 ml of diethyl ether was added thereto. The mixture was allowed to stand at 2°–8° C. The crystals formed were collected by filtration and washed with diethyl ether to obtain 53 g (yield: 88.9%) of the desired material having a melting point of 196°–198° C. (dec.).

$[\alpha]_D^{28} +5.9°$ (c=1.0, DMF)

Elemental Analysis

Calc'd for $C_{68}H_{77}O_{15}N_7Cl_2 \cdot 3/2H_2O$ (%): C 61.39, H 6.06, N 7.37; Found (%): C 61.43, H 5.88, N 7.62.

Amino Acid Analysis

Asp 1.00, Thr 1.68, Glu 1.08, Tyr 0.91, Phr 0.85

(26) Production of Docosapeptide Fragment of the Formula
BOC-Thr(Bzl)-Tyr[Bzl(Cl₂)]-Thr(Bzl)-Gln-Asp(OBzl)-Phe-Asn-Lys[Cbz(o-Cl)]-Phe-His-Thr(Bzl)-Phe-Pro-Gln-Thr(Bzl)-Ala-Ile-Gly-Val-Gly-Ala-Pro-NH₂
(amino acid sequence 10-31)

To 6.70 g of BOC-Asn-Lys[Cbz(o-Cl)]-Phe-His-Thr(Bzl)-Phe-Pro-Gln-Thr(Bzl)-Ala-Ile-Gly-Val-Gly-Ala-Pro-NH₂·3/2H₂O, 20 ml of TFA was added under cooling. The mixture was stirred under cooling for 5 minutes and at room temperature for 50 minutes, then concentrated in vacuo. During this time, 0.5 ml of an 8 N hydrogen chloride dioxane solution was added and the mixture concentrated to dryness in vacuo. After addition of diethyl ether, the precipitate was collected by decantation and dried. The powder was then dissolved in 30 ml of DMF. To the DMF solution, 0.46 g of HOBT and 4.44 g of BOC-Thr(Bzl)-Tyr[Bzl(Cl₂)]-Thr(Bzl)-Gln-Asp(OBzl)-Phe-OH·3/2H₂O were added. After addition of 20 ml of N-methyl-2-pyrrolidone, the mixture was cooled to below 0° C. To the solution, 0.62 ml of WSC was added and stirred at the same temperature. After several hours, the mixture was stirred at room temperature. After reaction for 3 days, 400 ml of ethyl acetate was added to the reaction mixture and the precipitate formed was collected by filtration, washed with ethyl acetate, comminuted in a 0.5 M acetic acid aqueous solution in a mortar, washed with water and collected by filtration. The precipitate was further washed with 0.5 M acetic acid and water and heated with 50 ml of methanol under reflux. After addition of ethyl acetate and diethyl ether, the mixture was allowed to stand. After cooling, the precipitate was collected by filtration and washed with ethyl acetate to obtain 9.2 g (yield: 89.4%) of the desired material having a melting point of 228°-234° C. (dec.).

$[\alpha]_D^{30} -27.0°$ (c=0.5, acetic acid)

Amino Acid Analysis

Asp 1.90(2), Thr 3.40(4), Glu 2.16(2), Pro 1.70(2), Gly 2.00(2), Ala 2.12(2), Val 0.93(1), Ile 1.03(1), Tyr 1.15(1), Phe 3.06(3)

EXAMPLE III

Production of Radioactive Iodine Labeled Hentriacontapeptide Tracer

To 5 μg of the hentriacontapeptide dissolved in a 0.01 M acetic acid aqueous solution (10 μg), 20 μl of a 0.5 M phosphate buffer (pH 7.5) and 1 mCi of a radioactive sodium iodide (Na¹²⁵I) aqueous solution having a pH of 8.5 to 9.4 were added. To this, 20 μg of chloramine T (dissolved in 40 μl of a 0.05 M phosphate buffer, pH 7.5) was added and reacted for 10 seconds, then 100 μg of sodium metabisulfite (dissolved in 40 μl of 0.05 M phosphate buffer, pH 7.5) was added to stop the reaction. Then, 40 μl of 5% BSA dissolved in physiological saline was added to the reaction mixture. The mixture was added to a column (1×15 cm) packed with Sephadex G-15 and eluted with a 0.05 M phosphate buffer containing 0.5% BSA. Fractions eluted at the beginning were collected and added to a column (1×40 cm) packed with Sephadex G-50 and eluted again with a 0.05 M phosphate buffer containing 0.5% BSA. A fraction eluted between 20-30 ml was collected and used as the tracer for RIA.

The radioactive iodine labeled hentriacontapeptide having a specific radioactivity of 100-160 μCi/μg was obtained in a yield of 350-550 μCi.

Figure 2:
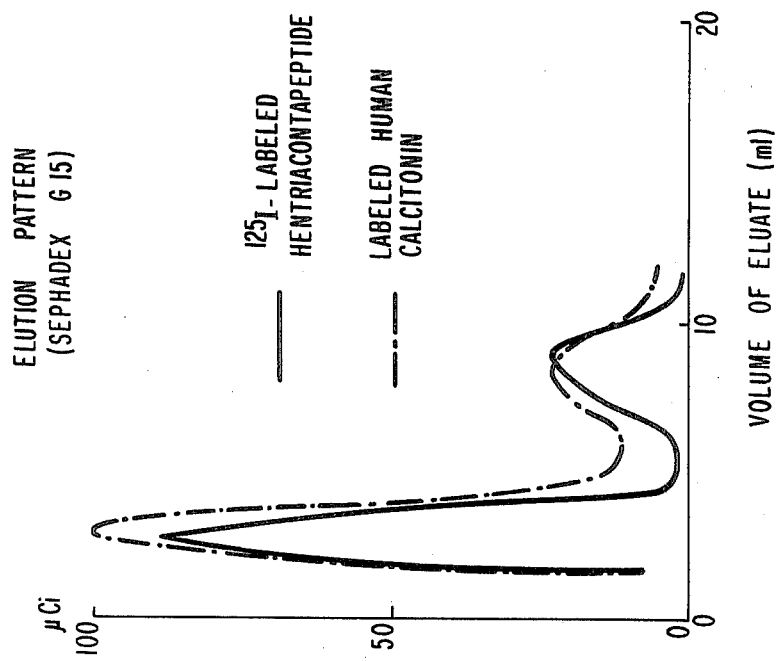
FIG. 2 and FIG. 3 show the pattern of elution.
Figure 3:
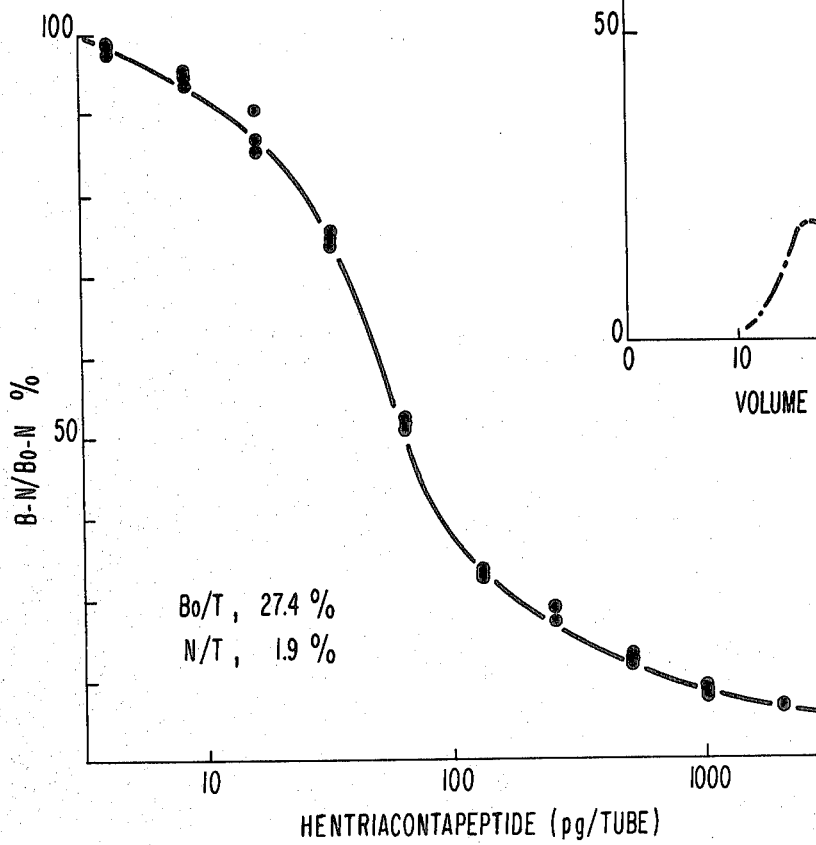
Figure 4:
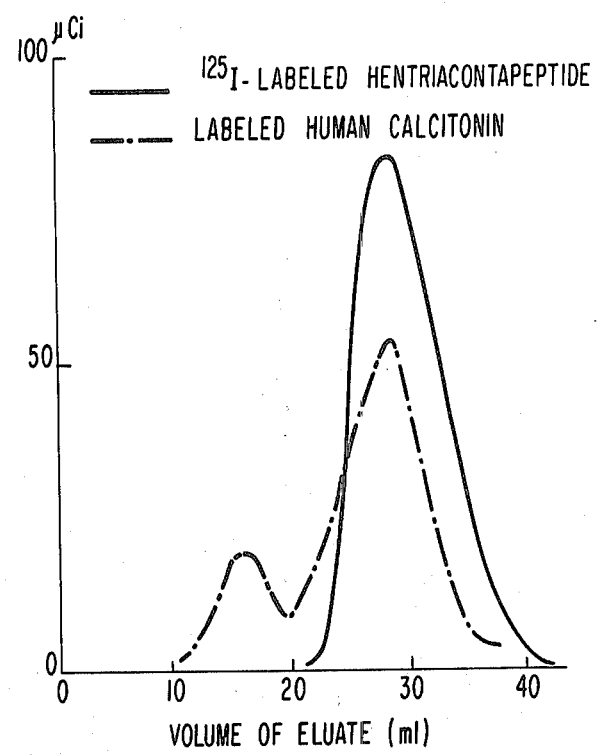
FIG. 4 shows a standard curve for radioimmunoassay.

FIG. 2 and FIG. 3 of the drawings show the pattern of the elution of the tracer in contrast with the pattern of labeled native human calcitonin.

In FIG. 2, when the products of labeling were eluted from a Sephadex G-15 column with a suitable eluant such as 0.1-1 N acetic acid or a phosphate buffer solution, two peaks can be seen in both the labeled native calcitonin and the hentriacontapeptide.

The first peaks indicate the tracer and the second peaks indicate free iodine.

On the other hand, when the material contained in the first main peaks above was each eluted from a Sephadex G-50 column (45 cm-60 cm) with a phosphate buffer solution containing 0.1% BSA (pH 7.0, μ=0.01), two different patterns were obtained as shown in FIG. 3.

The labeled native calcitonin shows two peaks and the first peak indicates labeled calcitonin polymers.

However, the labeled hentriacontapeptide shows only one peak. This means that the tracer provided by this invention (the labeled hentriacontapeptide) can be obtained in a pure form using a simple purification procedure.

EXAMPLE IV

Production of Antibody to Calcitonin

The hentriacontapeptide prepared as described in Example above (500 μg) was dissolved in 1 ml of physiological saline. Then, 1 ml of complete Freund's adjuvant was added thereto and emulsified. The emulsion was intradermally injected at multiple sites on the back and legs of a rabbit.

Four to ten weeks after the immunization, another 200-500 μg of the hentriacontapeptide emulsified in physiological saline and complete Freund's adjuvant as described above was administered to the rabbit using the multiple-site subcutaneous injection method above.

Ten to fourteen days after the booster injection, blood was collected from an ear vein to obtain antiserum to calcitonin.

EXAMPLE V

Radioimmunoassay Method

The serum sample (or standard solution) (100 μl) was placed in a test tube, and 0.5 ml of a 0.01 M phosphate buffer (pH 7.2 containing 0.3% BSA) and 0.1 ml of antiserum (diluted to about 2,500) produced in a rabbit with the hentriacontapeptide) were added thereto. The mixture was allowed to stand at 2° to 8° C. overnight. Then, 0.1 ml of (about 0.02 μCi) of ¹²⁵I-labeled hentriacontapeptide was added thereto and then allowed to stand at 2° to 8° C. overnight. Subsequently, 0.1 ml of goat antiserum produced by immunization with rabbit γ-globulin (the second antibody, about 7-fold dilution) was added thereto and allowed to stand overnight. The white precipitates formed were separated by centrifugation at 2000 xG for 15 minutes. After removing the supernatant, the radioactivity of the precipitates was counted.

Figure 5:
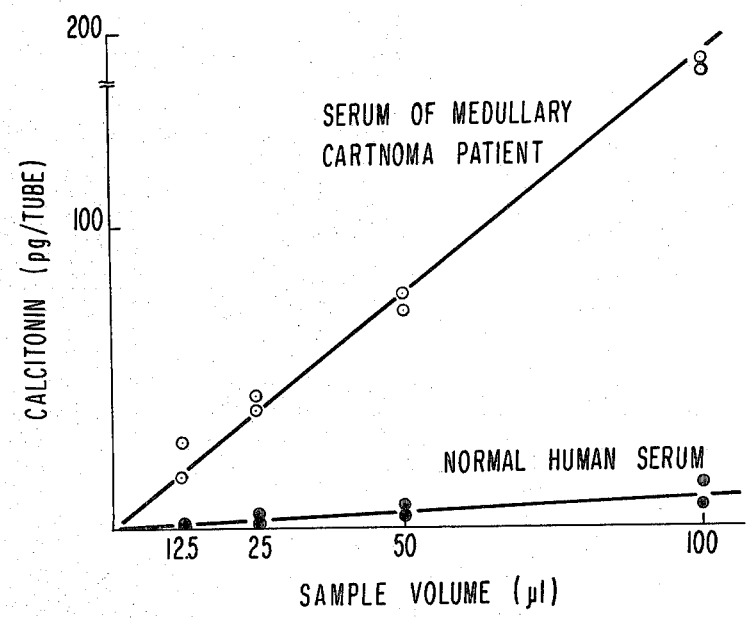
FIG. 5 shows the result of the determination of calcitonin in the serum sample of a patient with medullary carcinoma of the thyroid or a normal person.

FIG. 5 shows the calcitonin level determined in the sera of a normal person and a patient of medullary carcinoma of the thyroid.

While the invention has been described in detail and with reference to specific embodiments thereof, it will be apparent to one skilled in the art that various changes and modifications can be made therein without departing from the spirit and scope thereof.
What is claimed is:
1. A radioactive iodine labeled hentriacontapeptide of the formula (I):
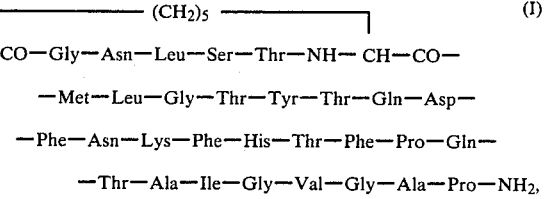
* * * * *